United States Patent
Harttig

[11] Patent Number: 5,939,470
[45] Date of Patent: Aug. 17, 1999

[54] DRY POLYMER BEAD PREPARATION

[75] Inventor: Herbert Harttig, Altrip, Germany

[73] Assignee: Boehringer Mannheim GmbH, Mannheim, Germany

[21] Appl. No.: 08/870,383

[22] Filed: Jun. 6, 1997

[30]    Foreign Application Priority Data

Jun. 7, 1996 [DE] Germany .............. 196 22 886

[51] Int. Cl.⁶ .......... C08K 9/10; G01N 33/546; B05D 3/00; B05D 7/02
[52] U.S. Cl. .......... 523/205; 523/204; 523/207; 523/210; 427/2.14; 427/222; 436/534
[58] Field of Search ................ 523/204, 205, 523/207, 210; 427/2.14, 222; 436/534

[56]    References Cited

U.S. PATENT DOCUMENTS

| | | | |
|---|---|---|---|
| 3,282,150 | 11/1966 | Burton | 355/8 |
| 4,001,360 | 1/1977 | Davis et al. | 264/49 |
| 4,233,169 | 11/1980 | Beall et al. | 252/62 |
| 4,245,026 | 1/1981 | Ziolo | 430/137 |
| 4,303,784 | 12/1981 | Fava et al. | 528/488 |
| 4,416,945 | 11/1983 | Solc et al. | 523/204 |
| 4,462,839 | 7/1984 | McGinley et al. | 523/204 |
| 4,483,920 | 11/1984 | Gillespie et al. | 435/6 |
| 4,495,216 | 1/1985 | Soerensen et al. | 523/204 |
| 4,880,870 | 11/1989 | Zimmermann et al. | 523/204 |
| 5,234,809 | 8/1993 | Boom et al. | 435/91 |
| 5,362,517 | 11/1994 | Flesher et al. | 523/204 |

FOREIGN PATENT DOCUMENTS

| | | |
|---|---|---|
| 0 535 937 | 4/1993 | European Pat. Off. . |
| 44 06 139 | 8/1985 | Germany . |

OTHER PUBLICATIONS

Hartig, H. et al., English abstract of DE 19520398, Dec. 12, 1996, Derwent WPIDS 97–035062.
Database WPI, Section CH, Week 9218, Dersent Publication Ltd., JP 04 089 834.
Patent Abstracts of Japan, vol. 018, No. 097, Jp 05 295 123.
Database WPI, Section CH, Week 7829, Derwent Publications Ltd., JP 53 065 489.
Fujimori et al, International Journal of Phamraceuticals 119, (1995) pp. 47–55, "Effect of magnetically controlled gastrice residence of sustained release tablets on bioavailability of acetaminophen".
Fujimori et al, S.T.P. Pharma Sciences 4 (6) 425–439, 1994, "Preparation of a magnetically–responsive tablet and confirmation of its gastric in beagle dogs."
International Publication No. WO 90/06045 published Jun. 14, 1990.

*Primary Examiner*—Peter A. Szekely
*Attorney, Agent, or Firm*—Nikaido Marmelstein Murray & Oram, LLP

[57]    ABSTRACT

The invention addresses a method of preparing a dry polymer bead preparation. To achieve this, the polymer beads are coated with a layer of an easily soluble substance which dissolves again in a liquid when the polymer beads are resuspended. The resuspension is thus largely free of agglomerates.

21 Claims, No Drawings

DRY POLYMER BEAD PREPARATION

Subject matter of the invention is a dry polymer bead preparation, a method of preparing such a polymer bead preparation, a method of concentrating a magnetic bead containing suspension, the use of sugars for coating polymer beads, the use of dry polymer bead preparations, and a method of detecting an analyte with the aid of a dry polymer bead preparation.

Plastic beads have been used in analytical procedures for the determination of analyte for some time. The presence of an analyte and/or the amount thereof can be concluded from the formation of an agglutinate and/or the amount of such agglutinate formed.

Recent development has seen the use of plastic magnetic beads in various embodiments as reagents in immunoassays as well as other tests. Owing to the presence of magnetic portions found in the beads, these beads can be separated from the suspension by applying magnetic forces. Regardless of the type of application used, it is necessary for the particles to be available as single particles avoiding the formation of aggregates. To date, such magnetic polymer beads are offered exclusively in the form of suspensions. These suspensions are obtained by directly polymerizing monomers. If necessary, the so obtained particles are subject to further treatment which is performed without removing the particles from the suspension.

However, a special storage problem has arisen in connection with suspensions of this kind. If, due to gravity, the magnetic beads sink down to the bottom of the bottle, they form a tightly packed clot. If the bottle is then turned upside down during transport, the clot is likely to dry out. During resuspension of the magnetic beads, it is not possible to again split the so formed aggregates completely into their individual particles. Even the application of ultrasound does not lead satisfactory results.

Object of the invention is therefore the preparation of a polymer bead preparation resuspensable without agglomerates.

Subject matter of the invention is a dry polymer bead preparation.

A polymer bead as understood in the invention is a particle obtained by polymerization. The preferred diameter of these polymer beads ranges between 0.1 and 100 $\mu$m, particularly preferred between 1.0 and 5.0 $\mu$m. The particles preferably have an essentially round shape and are known as beads. The preferred main component of a bead is an organic polymer. In addition to polymers obtained from one single monomer, this also covers polymers consisting of several monomers, i.e. copolymers. Possible monomers include polystyrene and polymethylmethacrylate. An example of such polymers are latex particles.

Polymer beads can be manufactured in known ways; e.g. dispersion of monomers in a liquid and start of polymerization depending on the type of polymerization reaction employed, i.e. light or polymerization starter. The manufacture of polymer beads is known to the expert, e.g. from L. B. Bangs (Amer Clin Prod Rev 7, 1, 22–26).

Although the invention allows to bring all kinds of polymer beads into an agglomerate-free, suspendable form, the description given here is geared towards the preferred case of magnetic polymer beads. Magnetic beads can principally be purchased in the form of a suspension, e. g. from Dynal AS. These beads are particles which essentially consist of an organic polymer rendered magnetic due to incorporated magnetic particles. The term magnetic includes not only ferromagnetic particles but also para- and super-paramagnetic particles with the latter being preferred.

Magnetic beads can be manufactured as described in EP-B-0 106 873.

In some analytical procedures these polymer beads are employed to selectively immobilize the analyte or analyte-binding substances. In these cases, it is known to modify the polymer beads in the suspension with the aid of reagents. This includes, for example, the application of a streptavidin layer on the particle surface which allows the binding of analytes or analyte-binding substances modified with biotin to the surface of the particle.

In accordance with the present invention, these particles are then coated with a layer of an easily soluble substance. The easy solubility of this substance refers to the solution in which the particles are to be resuspended at a later time. When analyzing body fluids, such solutions are essentially aqueous solutions. Easily soluble substances as understood in the invention are particularly sugars with a melting point lying above the conditions under which the dry polymer bead preparation is to be manufactured and stored. Suitable sugars include C-6 sugars and C-6 sugar-alcohols with mannite and trehalose being particularly preferred.

The coat of an easily soluble substance can be applied in numerous manners. It is, however, preferred to prepare a polymer bead suspension containing the easily soluble substance and spray the latter under conditions where liquid is withdrawn from the suspension. Such spray-drying procedures are known. When using commercially available suspensions, it suffices to add a certain amount of the soluble substance. This amount should be dosed such that the amount of soluble substance present is completely dissolved. The amount hence depends on the solubility of the soluble substance in the liquid of the suspension. In the case of sugars, an amount of e.g. 0.1 to 30 wt. –%, particularly preferred between 1 and 10 wt. –%, has proven to be expedient. The amount of soluble substance should be such that the layer surrounding each polymer bead has a thickness between 20 nm and 50 $\mu$m, particularly preferred between 0.1 and 5 $\mu$m. Whether or not the layer thickness is within the desired range when using a given amount of soluble substance can be easily determined with the aid of a microscope. For this purpose, the particles are preferably poured into a formed body and cross-sections are made from which the thickness of the particles and the coating can be read. So obtained polymer beads preferably have a smooth surface regardless of their original surface structure and provided the coating is thick enough, and also have a spherical geometry.

It is preferred to select low concentrations of magnetic polymer beads in the suspension during the spray-drying process. Suitable concentrations are those between 0.05 to 0.5 wt. –%. This results in the formation of droplets with or without a single magnetic particle. During drying the spraying tower, preferably 95% of the corresponding dried sugar particles or sugar particles contain no more than one single magnetic bead. The formation of doubles or triples, i.e. aggregates of two or three linked magnetic particles, is significantly reduced. Aqueous solutions are a particularly preferred for the preparation of polymer bead suspensions. The spray-drying process is continued until the resulting particles contain less than 1, preferably less than 0.1 wt–% free water. By heating the products obtained in the spray-drying process, it is possible to find out if the residual moisture satisfies the above conditions and determine a possible change in weight.

In a preferred manner the polymer beads of the invention can be poured.

It was surprising to see that when the powder-like mass obtained in the spray-drying is resuspended in a liquid containing the soluble substance, virtually no agglomerates of magnetic polymer particles form in the absence of a magnetic field. This also applies to non-magnetic polymer particles.

Depending on the amount of soluble substance used, non-bead-containing particles form in addition to coated polymer beads which essentially consist of the soluble substance. If an elevated percentage of soluble substance interferes, e.g. in analytical procedures, it is possible to separate especially the magnetic particle-free sugar particles. This is particularly easy in case of magnetic polymer beads. To achieve this, a suspension of the dry polymer bead preparation is prepared in a liquid in which the soluble substance does not dissolve; e.g. in case of sugars in low alcohols (1–3 C atoms) such as ethanol. Using a magnet, the magnetic particles are separated at the wall of the container and the remaining suspension is removed. After several washing steps with the liquid and removal or turning off of the magnet, a concentrate of polymer magnetic particles coated with soluble substance is obtained. The advantage of using lower alcohols is that they can be easily dried thus resulting in a dry powder. Resuspension of this powder in the liquid containing the soluble substance results in a suspension of polymer magnetic beads which are virtually free of aggregates and non-magnetic particles, containing in particular less the 5% aggregates.

Also subject matter of the invention is the use of sugars for coating polymer beads.

Another subject matter of the invention is the use of a dry polymer bead preparation in analytical procedures. Analytical procedures as understood in the invention are procedures where the amount of analyte bound to a given amount of polymer beads is determined. The expert is familiar with these methods, e.g. from L. B. Bangs (Particle-based Tests and Assay—Pitfalls, Problems and Possibilities in preparation; Bangs Laboratories, Carmel, Ind., USA, October 1990)

Subject matter of the invention is hence also a method of detecting an analyte from a liquid comprising the steps of preparing a dry polymer bead preparation, resuspending the dry polymer beads in a liquid, binding possibly present analytes to the polymer beads, and detecting the polymer bead-bound analyte. As described above, the dry polymer beads are preferably coated with a substance which is soluble in the liquid and are also magnetic.

The following examples explain the present invention in greater detail.

EXAMPLE 1
Preparation of Dry and Aggregate-Free Resuspendable Polymer Beads 25 ml of magnetic bead suspension M 280, manufactured by Dynal AS with a concentration of 10 mg beads/ml and 3 g of mannite and 3 g of water were mixed. Using a Niro-Atomizer-Spray-Drier, Minor, manufactured by Niro, Soeborg, Denmark, the resulting suspension was sprayed into a light brown powder. The yield was 2.1 g.

A small portion of the so obtained powder was resuspended in dist. water. When viewed under a light microscope, no aggregates were found.

EXAMPLE 2
Aggregation of Conventional Particles 0.5 ml of a magnetic bead suspension M 280 manufactured by Dynal AS were dried at 40° C. ambient air. The solid residue was taken up and resuspended in 10 ml dist. $H_2O$ and for 5 minutes treated in an ultrasonic bath. The resulting suspension contained large aggregates which were well visible under the light microscope.

EXAMPLE 3
Concentrating Dry and Aggregate-Free Resuspendable Magnetic Polymer Beads Appr. 50 mg of the resulting powder of example 1 were resuspended in app. 1.5 ml ethanol in an Eppendorf reagent vessel. A permanent magnet was applied to the wall of the vessel. The suspension became hot and a brown precipitate formed at the wall opposite the magnet. The remaining white suspension was pipetted off and the washing procedure was repeated with isopropanol.

The resulting precipitate was dried at ambient air.

The resulting dry powder was resuspended in dist. water. No aggregates were visible in the suspension under the light microscope.

What is claimed is:

1. Dry magnetic polymer beads which can be suspended in an aqueous liquid without substantial agglomeration in the absence of a magnetic field, comprising a plurality of polymer particles;

at least one magnetic particle incorporated with substantially each polymer particle; and a coating surrounding substantially each polymer particle, said coating comprised of a sugar which is readily soluble in an aqueous suspension liquid, wherein the coating has a thickness between 20 nm and 50 $\mu$m.

2. Dry polymer beads which can be suspended in a liquid without substantial agglomeration in the absence of a magnetic field, comprising (A) a plurality of polymer particles, substantially each of which polymer particles having at least one magnetic particles incorporated therein; and (B) a coating surrounding substantially each polymer particle, said coating being a sugar readily soluble in the suspension liquid.

3. The polymer beads of claim 2, wherein the sugar is water soluble.

4. The polymer beads of claim 3, wherein the sugar is mannite.

5. The polymer beads of claim 3, wherein the sugar is trehalose.

6. The polymer beads of claim 2, wherein the coating surrounding subtantially each polymer bead has a thickness between about 20 nm and about 50 $\mu$m.

7. The polymer beads of claim 2, wherein the coating surrounding substantially each polymer bead has a thickness between about 0.1 $\mu$m and about 100 $\mu$m.

8. The polymer beads of claim 7, wherein the coating surrounding substantially each polymer bead has a thickness between about 0.1 $\mu$m and about 5 $\mu$m.

9. A method of preparing the dry polymer beads of claim 2, comprising the following steps (1) providing polymer beads, substantially each of which polymer bead having at least one magnetic particle incorporated therein;

(2) preparing a suspension of said polymer beads in a liquid containing a sugar for coating the beads, wherein said sugar is readily soluble in the liquid;

(3) spray-drying the suspension to remove the liquid from the remainder of the suspension, thereby producing a product comprising droplets having at least one polymer bead therein; and thereafter (4) removing from the product any droplets not having at least one polymer bead therein to obtain dry polymer beads coated by the sugar.

10. The method of claim 9, wherein the spray-drying of the suspension is performed in such a way until more than 95% of the droplets contain a single polymer bead.

11. The method of claim 9, wherein the liquid in which the polymer beads are suspended contains an amount of the sugar between about 0.1% and about 30% by weight prior to the spray-drying.

12. The method of claim 11, wherein the liquid in which the polymer beads are suspended contains an amount of the sugar between about 1% and about 10% by weight prior to the spray-drying.

13. The method of claim 9, wherein the sugar is water soluble.

14. The method of claim 13, wherein the sugar is mannite.

15. The method of claim 13, wherein the sugar is trehalose.

16. A method of recovering the magnetic polymer beads of claim 2 from a suspension of such beads, comprising (1) applying a magnetic field to the wall of a container containing a suspension of the polymer beads of claim 2 in a liquid, wherein said sugar coating does not dissolve in said liquid, to immobilize the polymer beads at the wall of the container; and thereafter (2) separating the liquid from the polymer beads, to provide dry magnetic polymer beads.

17. The method of claim 16, wherein said suspension further comprises particles which do not have polymer beads therein, and such particles are separated with the liquid from the magnetic polymer beads.

18. The method of claim 16, wherein said liquid is a C1–C3 alcohol.

19. In a method of detecting an analyte in a liquid, comprising the steps of (1) adding polymer beads in the liquid containing the analyte to be determined, wherein said analyte binds said polymer beads;

(2) separating the liquid from the polymer beads and analyte bound thereto; and thereafter (3) detecting the analyte;

the improvement comprising:

substantially preventing the agglomeration of the polymer beads in the liquid by using the polymer beads of claim 2, wherein the coating dissolves when the polymer beads are suspended in the liquid.

20. The method of claim 19, further comprising, after the analyte binds to the polymer beads but prior to separating the liquid from the polymer beads, applying a magnetic field to the liquid to retain the polymer beads and analyte bound thereto.

21. The method of claim 20, wherein the detecting step involves determining the amount of the analyte bound to a given amount of the polymer beads.

* * * * *